United States Patent
Parekh et al.

(10) Patent No.: US 7,153,495 B2
(45) Date of Patent: *Dec. 26, 2006

(54) FRAGRANCE FRIENDLY AND COST EFFECTIVE ANTIPERSPIRANT ACTIVES AND METHOD OF MAKING THE SAME

(75) Inventors: Jawahar C. Parekh, Livingston, NJ (US); Pradip T. Amin, Edison, NJ (US); Chung Teck Shin, Livingston, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/865,397

(22) Filed: Jun. 10, 2004

(65) Prior Publication Data

US 2005/0276773 A1 Dec. 15, 2005

(51) Int. Cl.
*A61Q 15/00* (2006.01)
*A61K 8/00* (2006.01)
*A61K 8/02* (2006.01)

(52) U.S. Cl. .................... 424/65; 424/66; 424/68; 424/400; 424/401

(58) Field of Classification Search .................. 424/65, 424/66, 68, 400, 401
See application file for complete search history.

(56) References Cited

U.S. PATENT DOCUMENTS

| | | |
|---|---|---|
| 2,814,585 A | 11/1957 | Daley |
| 2,854,382 A | 9/1958 | Grad |
| 2,906,668 A | 9/1959 | Beekman |
| 3,405,153 A | 10/1968 | Jones |
| 3,979,510 A | 9/1976 | Rubino |
| 4,017,599 A | 4/1977 | Rubino |
| 4,331,609 A | 5/1982 | Orr |
| 4,775,528 A | 10/1988 | Callaghan |
| 4,871,525 A | 10/1989 | Giovanniello |
| 4,900,534 A | 2/1990 | Inward |
| 5,114,705 A | 5/1992 | Callaghan |
| 5,225,187 A | 7/1993 | Carmody |
| 5,296,623 A | 3/1994 | Katsoulis |
| 5,333,751 A | 8/1994 | Santucci |
| 5,486,347 A | 1/1996 | Callaghan |
| 5,589,196 A | 12/1996 | Callaghan |
| 5,718,876 A | 2/1998 | Parekh |
| 5,939,057 A | 8/1999 | Provancal |
| 5,955,064 A | 9/1999 | Giovanniello et al. |
| 6,066,314 A | 5/2000 | Tang |
| 6,074,632 A | 6/2000 | Shen |
| 6,375,937 B1 | 4/2002 | Chopra |
| 6,436,381 B1 | 8/2002 | Carrillo |
| 6,451,296 B1 * | 9/2002 | Li et al. .................. 424/66 |
| 6,960,338 B1 * | 11/2005 | Li et al. .................. 424/65 |
| 2003/0138389 A1 | 7/2003 | Klug |

FOREIGN PATENT DOCUMENTS

| | | |
|---|---|---|
| GB | 1353916 | 5/1974 |
| GB | 2075289 | 11/1981 |
| WO | WO 01/56539 A1 | 8/2001 |
| WO | WO 03/007903 A1 | 1/2003 |

OTHER PUBLICATIONS

Brune, M., et al., "Iron Losses in Sweat", The American Journal of Clinical Nutrition, vol. 43, Mar. 1986, pp. 438-443.
Foy, H. and Kondi, A., "Anaemias of the Tropics", The Journal of Tropical Medicine and Hygiene, vol. 60, May 1957, pp. 106-118.
Green, R., et al., "Body Iron Excretion in Man", American Journal of Medicine, vol. 45, Sep. 1968, pp. 336-353.
Hoffman, H.M. and Ansari, R., "Fragrancing of Antiperspirant Products," Reheis Inc. Report 11, 1983.
Jacob, R.A., "Whole Body Surface Loss of Trace Metals in Normal Males," The American Journal of Clinical Nutrition, vol. 34, Jul. 1981, pp. 1379-1383.
Johnston, F.A., et al., "Perspiration as a Factor Influencing the Requirement for Calcium and Iron," Journal of Nutrition, vol. 42, Jun. 1950, pp. 285-296.
Landa, A. and Makin, S., "Iron Sequestration on Skin: A New Route to Improved Deodorancy," 22nd IFSCC Congress, Edinburgh, Scotland, 2002.
Murphy, T.D. and Levine, M.J., "Analysis of Antiperspirant Efficacy Test Results," Journal of the Society of Cosmetic Chemists, vol. 42, May/Jun. 1991, pp. 167-197.
Nicoll, S., "Fragrance Stability in Three Cosmetic Applications," C&T, vol. 114 No. 7, Jul. 1999, pp. 59-63.
Vellar, O.D., "Studies on Sweat Losses of Nutrients," Scandinavian Journal of Clinical and Laboratory Investigation, vol. 21, 1968, pp. 157-167.
"Cult of Personality,"Soap, Perfumery & Cosmetics, Jul. 2001, pp. 18-21.
IBC Advanced Technologies Inc. Brochure on Innovation Molecular Recognition Products.
"Inspired to Prespire, Gillette Uncovers Sweat," The Gillette Company web site at www.gillette.com/women/features/ss_inspired.htm.

* cited by examiner

*Primary Examiner*—Shelley A. Dodson
(74) *Attorney, Agent, or Firm*—Arthur J. Plantamura

(57) ABSTRACT

A cost effective process is provided for making stable, efficacious, amino acid and polyhydric alcohol free concentrated aqueous aluminum zirconium salt solutions. Absence of amino acid, low iron content and low trace metal impurity levels improve compatibility with fragrances and minimizes the probability of the product color change and possibly fabric staining significantly. The novel aluminum zirconium actives also minimize iron contribution to underarm area that supports growth of microflora which is responsible for axillary malodour by the biotransformation of nonodorous precursors present in perspiration. The astringent complexes of the present invention may be obtained in solution or dry powder form. As a result, the complexes are satisfactory for use in any of wide variety of conventional antiperspirant forms.

31 Claims, 1 Drawing Sheet

FRAGRANCE FRIENDLY AND COST EFFECTIVE ANTIPERSPIRANT ACTIVES AND METHOD OF MAKING THE SAME

BACKGROUND OF INVENTION

The invention relates to novel compositions and a process for making fragrance friendly aluminum zirconium salts that are commonly considered active antiperspirant materials and are covered by FDA OTC Final Monograph as Category I.

The antiperspirant and deodorant market offers a wide diversity of products to meet consumer needs. The physical forms of antiperspirants vary greatly. They include aerosols, pump sprays, squeeze sprays, creams, roll-ons, suspension roll-ons, deodorant sticks, clear gels, soft solids, etc. Different physical forms of final formulations require that antiperspirant actives meet certain specific chemical or physical properties or both to achieve the desired results. Prominently in the hierarchy of consumer wants is long lasting control of fragrance and wetness. Consumers also want their antiperspirant to have excellent sensory properties on application and certain aesthetics.

The reasons for such a variety of individual preference products is that the manufacturers increasingly turn to market segmentation to increase their total share of dollar sales and today's customers have sophisticated expectations. For example, clarity remains a market force in the personal care industry as consumers associate clarity with lack of unsightly white residue on skin and clothing. Given these circumstances, it is evident that growth of individual brands must come primarily through product improvement. This can be achieved either by improving product aesthetics or antiperspirancy, or both. Prospects for such improvements have provided an impetus for the development of newer actives and their modifications to meet specific formulation requirements.

The antiperspirant product group is probably the most demanding in terms of creative (aesthetic) and technical implications when it comes to creating fragrances that are compatible. (Hoffman, H. M. and Ansari, R., *Fragrancing of Antiperspirant Products*, Reheis Report 11, 1983).

Fragrance is an important part of antiperspirant and deodorant appeal. According to a research[1] (*Cult of Personality*, Soap, Perfumery & Cosmetics, July 2001, pp. 18–21). Half of all consumers cite fragrance as an important reason for choosing when purchasing antiperspirant devices. Young consumers in particular are influenced by fragrance.

Fragrance plays a key role in personal care products such as deodorants and antiperspirants. It attracts customer interest, inspires the first purchase, retains brand loyalty, communicates sensory perception that the product is doing its job and gives the overall feeling of confidence and personal freshness.

Fragrance is highly important in the development of any new product, while a fragrance may not contribute to the properties of an antiperspirant product, it can by its very nature, influence the consumer's expectations of the product's performance. A successful fragrance must coordinate with the product's attributes. Its initial impact, continuing impression, performance and stability are crucial in ensuring a harmonious commercially attractive product. Thus, good understanding of chemical and physical characteristics of both the fragrance and product and possible interactions are essential to a successful antiperspirant such as a a clear antiperspirant stick that is introduced in the market place. In one situation, for example, dibenzylidene sorbitol as a gelling agent in an antiperspirant found it degraded in the presence of acidic antiperspirant and generated a not too pleasing cherry-almond aroma particularly noticeable on storage due to the release of benzaldehyde. Since then, several attempts have been made to address the issue of the instability of this gelling agent and how it can be stabilized while also retaining the efficacy of incorporated fragrances.

As noted in Nicoll (Nicoll, S., *Fragrance Stability in Three Cosmetic Applications,* C&T, Vol. 114, No. 7, July 1999, pp. 59–63), when the fragrance is added to the base of a product any of the following reactions may occur:
the product discolors,
off-odors develop in the product,
fragrance is short lived or disappears with time,
fragrance looses its ability to mix with the base either initially or progressively.

Many reactions can occur when metal ions are present in the product. These metals can develop highly colored oxides when combined with fragrance ingredients leading to product discoloration. Color is one of those issues that can be quite frustrating. Often the color change may not be significant but visual change draws a strong customer response, e.g., if the product does not look good, it cannot be good. Color change can be caused by a number of factors for example citrus and fruit fragrances cause color with antiperspirant active due to oxidation or hydrolysis of esters. Oxidation can be further catalyzed by iron or other materials.

Although antiperspirants and deodorants are two different product groups, they are often grouped together. In fact, the two are quite different in their mode of action and their formulation, requiring different technical considerations. These differences have far reaching implications when it comes to fragrancing these products.

The function of deodorants is essentially to mask underarm odor with fragrance and inhibit the proliferation of bacteria responsible for the sweaty smells. In many cases, a product sold as a deodorant may solely be based on an alcoholic solution of the fragrance and a bactericide. The medium to fragrance is usually mild and the perfumer is able to concentrate largely on the aesthetics in the selection of raw materials for the creation of fragrances. On the other hand, the fragrancing of antiperspirants is very different and hedonically pleasing fragrances for antiperspirants are challenging.

Antiperspirants inhibit eccrine perspiration and thereby reduce wetness; the aluminum salts and aluminum zirconium complexes, the active ingredients of antiperspirants, are also known to have antibacterial activity and must, therefore, inhibit the proliferation of bacteria responsible for the degradation of apocrine sweat, giving rise to malodorous fatty acids and other volatile nitrogeneous compounds. Whatever malodor problem that might remain is supposed to be taken care of by the fragrance. The antiperspirant then becomes a deodorant too and the fragrancing becomes a crucial factor in determining the consumer acceptability of the product.

The majority of antiperspirants use aluminum chlorohydrate or Al/Zr products having Al/Zr ratio from 2:1 to 10:1 and metals to chloride ratio of 0.9:1 to 2.1:1 in micronized dry powder form or solutions depending upon the final product form. All these preparations work under acidic conditions (e.g., a 20% w/w solution of aluminum chlorohydrate has an approximate pH of 4.0), rendering many fragrances unstable in the base. As the metals/anion ratio decreases, the product becomes more efficacious, more acidic and less compatible with fragrances. To compensate for acidity, usually higher amount of glycine is employed which makes the product more expensive. Acidity could also have an effect on its compatibility with fragrance as a source of primary amine, like glycine is likely to react with aldehydes present in fragrance and form imines which impart color to the product. This instability causes changes in odor and induces discoloration of the final formulation over a period of time.

Since a fragrance is a complex mixture of blend of aromatic materials of natural and synthetic origin, it is very difficult to ensure that all the ingredients present will be stable and free from degradative changes induced by the pH of the medium and other changes catalyzed by the metals present. In general, it is recommended that natural oils be avoided, since they invariably contain a great number of chemicals of differing functionalities, making it almost impossible to predict the behavior of the individual components once incorporated into the base. According to Hoffman and Ansari, exception to this is probably the woody complexes based on Patchouly, Cedarwood and Sandalwood. Another point of importance is that aluminum and zirconium salts almost always contain iron as an impurity which complexes with fragrance materials bearing phenolic functionality and causes serious discoloration problems. Stating it differently, the antiperspirant base imposes considerable limitations on the use of fragrance raw materials. It is noted that aldehydic fragrances have dominated this segment of the market; probably the reason is that many aldehydes are fairly stable in the base media. Most of other known types found on the market are only marginally stable.

Although the fragrance industry has provided the formulators of antiperspirants with fragrances that are stable and have consumer acceptance, consumers desire for new fragrances are ever increasing.

Most widely used aluminum zirconium antiperspirants usually contain primary amino acids like glycine as buffers to avoid gelling of aluminum zirconium aqueous system. The source of primary amines present in antiperspirant active can react with aldehydes present in fragrance to form a Schiff base that is usually highly colored. This change in color can be problematic especially because it is usually catalyzed by light or heat exposure.

In summary, it can be stated that antiperspirant bases are acidic, cationic and contain metal ions which can catalyze the degradation of many fragrance ingredients causing odor changes and discoloration. In perfuming, the pH of the antiperspirant product plays an important role. Antiperspirants are typically in the pH range of 3.5 to 4.5 and perfumes are more unstable at lower pH. Many perfume materials react with the aluminum and aluminum zirconium actives used in antiperspirant. This can lead to a change in the odor of the perfume or to a discoloration of the product. Imines are formed when aldehyde reacts with a primary amine to release a water molecule. The glycine, a common component present in aluminum zirconium complexes, is a primary source of amine and can react with fragrances to give a color.

Iron is usually present in USP grade antiperspirant active as an impurity at a fairly high level up to 50 ppm in solution to 125 ppm in powders. Pink coloration of an antiperspirant product is usually traced directly to metal interactions, primarily iron. Other metals such as Mn, Cu, Co, Cr or Ni can cause color generation if they are present in significant amounts.

It has been well established that axillary malodour is caused by biotransformation of non odorous precursors present in apocrine sweat and sebum by the axillary microflora. To counter this, deodorants normally contain bactericides. However, after the initial kill of bacteria, the surviving cells grow, producing a concomitant rise in axillary odor. Long lasting deodorant effect is achievable only if bacterial growth is inhibited for an extended period such as by a controlled release of a bactericide. Another approach is to inhibit bacterial growth by nutrient deprivation, primarily that of iron Fe(III) as has been proposed by L. Andrew and Stephen Makin (*Iron Sequestration on Skin: a new route to improved deodorancy*, $22^{nd}$ IFSCC Congress, Edinburgh 2002). The content of that publication and of the patent disclosure in WO 03/007903A, titled "Deodorant Compositions Comprising A Transition Metal Chelator and A Silicon Fluid", are incorporated herein by reference in their entirety. Based on reported research the indication is that the deprivation of iron Fe(III) has the most profound effect on bacterial growth.

However, it should be recognized that while reduction in iron contribution by antiperspirant is beneficial, it does not deprive microflora of all the iron as there are two other source of iron from the skin, namely losses of iron in sweat and losses of iron in desquamated epithelial cells. The latter are probably fairly constant in the single individual and independent of the amount of sweat lost whereas sweat iron loss vary considerably. Various studies have been reported in the literature concerning the loss of iron and other trace metals through the skin. Concentration of iron values reported in the sweat vary considerably depending upon how the sweat was collected, analytical techniques used and whether the sweat was collected under thermal stress or at room temperature, etc. The following references provide useful insight into trace metal losses through skin. Of particular interest is the iron in cell-free sweat in the underarm area. Brune, M.; Magnusson, B.; Persson, H. and Hallberg, L. reported their findings on the loss of iron in whole body cell-free sweat in eleven healthy men in an article titled *Iron Losses in Sweat* (Journal of American Clinical Nutrition, Vol. 43, March 1986, pp. 438–443). In this study a new experimental design was used with a very careful cleaning procedure of the skin and repeated consecutive sampling periods of sweat in a sauna. The purpose was to achieve a steady state of sweat iron losses with minimal influence from iron originating from desquamated cells and iron contaminating the skin. Iron loss was directly related to the volume of sweat lost and amounted to 22.5±2.29 µg of iron/liter of sweat. The findings indicated that iron is a physiological constituent of sweat and the iron content of cell rich, compared to cell free, sweat was about five (5) times higher.

Green, et al., (*Body Iron Excretion in Man, A Collaborative Study*, American Journal of Medicine, Vol. 45, 1968, pp. 336–53) reported sweat iron losses in laundry workers with heavy sweat losses. The calculations of sweat iron losses were based on the rate of decline in specific activity of $^{55}$Fe over several years. The average extra iron loss due to the perspiration (from the whole body) calculated from that study was about 0.1 mg/day.

On its web page titled Inspired to Perspire, Gillette Uncovers Sweat Gillette has reported several of the findings about sweat from its experts as follows: (1) the average amount of perspiration from underarms in one hour at room temperature equals 200 mg; (2) the average amount of perspiration from underarms in one hour at room temperature during emotional stress equals 700 mg; (3) underarms are the top sweat producing areas of the body; (4) men have a much higher sweat rate than women; (5) the usage rate of antiperspirant and deodorant varies with the age group; (6) men use an antiperspirant or deodorant an average of 7.9 times a week and women 8.3 times a week; (7) young men and women use antiperspirants and deodorants more frequently than any other group; (for example, women age 13–17 use 10.3 times/week and men age 15–17 use 9.8 times/week); and (8) more than 90% of men and women use a deodorant or an antiperspirant. Thus, it is safe to assume that on an average antiperspirant is used at least once/day.

Using the information of iron concentration in cell free sweat as determined by Brune et al., and the average amount of perspiration from underarms reported by Gillette, iron contribution by cell free sweat in underarm areas is computed to be 0.108 µg /day.

Maximum iron content of a typical USP grade antiperspirant powder can be 125 ppm and average usage rate of an antiperspirant product per application per underarm is about 0.4±0.05 gm. According to the final OTC monograph issued by FDA in June 2003, maximum anhydrous solids content of aluminum zirconium active in an antiperspirant formulation can be 20%. Thus, the maximum iron contribution by Al/Zr antiperspirant salt to underarm can be about 28.8 µg/day. Assuming an iron content of 70 ppm in Al/Zr active iron contribution could be about 16 µg/day.

While the exact amount of iron contribution by sweat and desquamation in the underarms area is not known the aforementioned computed numbers give some perspective as to the amount of iron involved and whether reduction in iron content of the active would help improve deodorancy of antiperspirant product or not. It is not known whether the iron from the active is readily available to the microflora as it is from the iron carrier protein transferring, present in eccrine sweat. Since the iron contribution by antiperspirant appears to be significant, reduction in its value is hypothesized to improve deodorancy of the final product assuming that iron from the active is available as a nutrient to the axillary microflora.

Thus, the objective is to make aluminum zirconium actives with low trace metal impurities, low iron, glycine free and at least equal in efficacy to the products currently used.

Accordingly, to improve fragrance compatibility it is preferred to have an aluminum zirconium active without primary amine, with low or no iron content and very low Mn, Co, Cr, Cu and Ni levels.

Because the antiperspirant market is flooded with a variety of products and this imposes many different requirements on antiperspirant actives and finished formulations and because almost all forms of antiperspirant formulations are scented compatibility of different actives in different product forms with fragrances is extremely important and the nemesis of all product marketers is color change.

With reference to the prior art patents, aluminum zirconium antiperspirant salts have been known since about 1954; numerous patents have been issued for the processes and compositions of making these salts. Patent documents which are cited in connection with the disclosed invention are U.S. Pat. No. 2,814,585 (Daley), U.S. Pat. No. 2,854,382 (Grad), GB 1,353,916 (Bolich), GB 2,075,289 (Mackles), U.S. Pat. No. 3,979,510 (Rubino), U.S. Pat. No. 4,017,599 (Rubino), U.S. Pat. No. 4,331,609 (Orr), U.S. Pat. No. 4,775,528 (Callaghan), U.S. Pat. No. 4,871,525 (Giovenniello), U.S. Pat. No. 4,900,534 (Inward), U.S. Pat. No. 5,225,187 (Carmody), U.S. Pat. No. 5,296,623 (Katsoulis), U.S. Pat. No. 5,33,751 (Curtin), U.S. Pat. No. 5,718,876 (Parekh), U.S. Pat. No. 6,066,314 (Tang), U.S. Pat. No. 6,375,937 (Chopra), U.S. Pat. No. 6,436,381 (Carrillo), etc.

Some of these aluminum zirconium antiperspirant salts are described as having enhanced efficacy, which means that they provide greater sweat reduction than conventional antiperspirant salts. The enhanced efficacy salts are typically differentiated from conventional antiperspirant salts by reference to the various aluminum peaks that can be identified when the salt is analyzed by size exclusion chromatography, typically HPLC. For more discussion on peak assignments of HPLC chromatography reference is made to copending application Ser. No. 10/807,996 filed Mar. 24, 2004.

A common aspect of all the patents cited is that they use mostly neutral amino acid or salts of amino acid to avoid gelling and to reduce acidity when basic aluminum halides and zirconium salts, like zirconium oxychloride ($ZrOCl_2$) or zirconium hydroxychloride ($ZrO(OH)Cl$) solutions, are combined to create more efficacious aluminum zirconium antiperspirants. In some of the recent patents, for example, U.S. Pat. No. 6,066,314 discloses post addition of glycine to aluminum zirconium salts containing glycine in an amount of 1:1.2–1.5 of zirconium to amino acid on a weight weight basis. Marginal, if any, associated increase in efficacy is expected. However, the product is more expensive. Also, U.S. Pat. No. 6,375,937 comprises aluminum zirconium salts which have a metal to chloride molar ratio in the range of 0.9–1.2:1 and glycine:zirconium molar ratio greater than 1.3:1 and more particularly greater than 1.4:1. Such excessive amounts of glycine increases cost of the product significantly and probably make the product less compatible with fragrances. In U.S. Pat. No. 2,814,585 Daley discloses (column 3, lines 50 to 70) that high concentration of the amino acids in aluminum zirconium antiperspirant compositions have a deleterious effect upon the efficacy of the composition. Moreover, antiperspirant preparations containing such large amount of amino acids are not economically attractive from a marketing standpoint.

Accordingly an object of the invention is to develop a process for making aluminum zirconium antiperspirant salt over the entire range covered by the OTC Monograph without the requirement of inclusion of any amino acid or salts of amino acids or other buffers.

U.S. Pat. Nos. 4,775,528; 5,114,705; 5,225,187; 5,486,347; 5,589,196; 5,955,064; 5,939,057; 6,066,314; 6,074,632; 6,451,296 B1; and EP 0633203 A1, and WO 01/56539 disclose aluminum zirconium antiperspirant compositions containing either both glycine and polyhydric alcohol or only polyhyric alcohol. With respect to formulations containing solely polyhydric alcohol the prior art indicates that stable and efficacious antiperspirant is obtained by eliminating glycine and replacing it with polyhydric alcohol. While the replacement of glycine by polyhydric alcohol in aluminum zirconium yields efficacious antiperspirant, it also tends to introduce an undesirable tackiness to the antiperspirant active and formulations of this kind have limited product application.

Thus, it is highly desirable to have a stable and effective aluminum zirconium active which is free of glycine as well as polyhydric alcohol.

In U.S. Pat. No. 2,906,668, Beekman disclosed a process for preparing aluminum/zirconium complex with aluminum to zirconium atomic ratio in the range of 2 to 10; but in both the examples cited, a gel was formed which was changed to opalescent or cloudy liquid by heating. Gelling is due to polymerization of zirconium species and this renders the product to be less efficacious. Daley, in U.S. Pat. No. 2,814,585 discloses that prevention of gelling of antiperspirant preparation is extremely important since gels have been found to have limited antiperspirant properties so as to be considered useless from a practical standpoint.

In U.S. Pat. No. 3,405,153 Jones disclosed a process for preparing aluminum-zirconium complex by adding zirconium oxychoride to hot aluminum chlorohydroxide and the gel that was formed was said to be essentially dissolved with prolonged heat and agitation and reflux which yielded cloudy solution. Thus it suffers from the same limitations as those for U.S. Pat. No. 2,906,668 noted above.

In U.S. patent application Ser. No. 10/625,038 is disclosed a process to make aluminum zirconium salts without amino acid and polyhydric alcohol, but the process is not capable of producing all the aluminum zirconium salts approved by FDA under the OTC Final Monograph issued on June 2003. This is demonstrated on the FIGURE of the accompanying drawing. Only products covered by the shaded area in FIG. 1 can be made using the system described in that patent application. Specific products that can be prepared using the process of the above mentioned patent application include aluminum zirconium tetrachlorohydrate with Al/Zr atomic ratio from about 2 to 6 and metal/chloride atomic ratio from about 0.9 to 1.25; aluminum/zirconium octachlorohydrate having Al/Zr atomic ratio from about 6 to about 10 and metal to chloride atomic ratio about 0.9 to about 1.5 and aluminum zirconium pentachlorohydrate having Al/Zr atomic ratio from about 6 to 10 and metal to chloride atomic ratio of about 1.51 to about 1.65. According to the novel process of the present invention, it has been discovered that all of the aluminum zirconium products under FDA OTC Final Monograph issued on June 2003, i.e., those encompassed by the FIGURE of the drawing can be made. It is important to note that the two most widely used aluminum zirconium antiperspirant are aluminum zirconium trichlorohydrex (with Al/Zr ratio of 3 to 6 and M/Cl ratio of 1.51 to 2) and aluminum zirconium tetrachlorohydrex (with Al/Zr ratio in the range of 3–5 and metals to chloride ratio of 1.35 to 1.5) and with respect thereto, process of U.S. patent application Ser. No. 10/625,038 has very limited application. Also, that application does not address the issue of color formation (fragrance compatibility) achieved by the novel product of the present invention in which iron and trace metal (Co, Cr, Ni, Mn and Cu) levels are closely controlled to minimize color formation with the fragrances. Fragrances are more stable and compatible with higher metals to chloride ratio aluminum zirconium products, but such products are incapable of being made with the process of U.S. patent application Ser. No. 10/625,038 as shown by FIG. 1. In summary, the novel process of the present invention is unique in that it facilities formulation of the entire range of very low iron aluminum zirconium antiperspirant salts that fall within the scope of the OTC Final Monograph without incorporating amino acid or polyhydric alcohol; which are cost effective; which minimize the probability of the final product's color change; which are more compatible with fragrance; and which improve deodorancy by reducing iron contribution to underarm area.

U.S. Patent Application Publication No. 2003/0138389 A1 discloses a deodorant antiperspirant comprising an aluminum chlorohydrate with an iron content of less than 20 ppm on a dry basis having improved efficacy and deodorancy for low iron product (10 ppm) compared to high iron product (80 ppm). The disclosure of that patent application is incorporated herein in its entirety by the reference. No disclosure is contained in that application which deals with color formation or fragrance compatibility for low iron glycine free aluminum zirconium product or regarding the preparation of more cost effective amino acid free aluminum zirconium products.

U.S. Pat. No. 6,451,296 B1 discloses that low molecular weight aluminum species as measured by HPLC Band IV (or peak 5) lead to more efficacious products. However, it is important to note that U.S. Pat. No. 6,451,296 B1 teaches use of high concentration of polyhydric alcohol during the reaction phase to avoid polymerization of zirconium species and does not teach how to make low iron low trace metal, glycine free and cost effective aluminum zirconium salts which are more compatible with fragrances. Also the product of this patent tend to be tacky and have limited application. In Carrillo, et al., U.S. Pat. No. 6,436,381 improved efficacy is correlated with low metal to chloride (0.9:1 to 1:1) aluminum zirconium products with peak 5 (or Band IV). The disclosure of U.S. Pat. No. 6,436,381 does not embrace glycine free aluminum zirconium salts over the metal/chloride ratio range greater than 1.1. The requisite process parameters and composition of the present invention are outside those employed in the patent.

None of the foregoing referenced prior art discloses or teaches the process of the present invention: of making low iron (less than 30 ppm, preferably less than 20 ppm, more preferably less than 10 ppm and most preferably less than 5 ppm) aluminum zirconium antiperspirant salts without amino acid or amino acid salt or polyhydric alcohol; having very low trace metal (Co, Cr, Ni, Mn, and Cu) impurity level (less than 2 ppm and more preferably less than 1 ppm) and which are fragrance friendly, very cost effective and very efficacious. Because zirconium and amino acids or salts of amino acids are the most expensive ingredients in any aluminum zirconium antiperspirant actives, the elimination of glycine and/or its salts and increasing the Al/Zr ratio from 3.5–4 to 7–8 without sacrificing efficacy makes the novel product of this invention most cost effective and attractive from marketing standpoint. Where efficacy comparable to that of enhanced efficacy salt is desired, it can be achieved by lowering the concentration of basic aluminum chloride to about 15–20 wt % and lowering Al/Zr ratio from 7–8 to 3–4 range. Addition of highly acidic $ZrOCl_2$ or $ZrO(OH)Cl$ result in depolymerization of aluminum species resulting in higher concentration of aluminum species in peaks II, IIII and IV.

SUMMARY OF THE INVENTION

The present invention is directed at aluminum zirconium actives, with their unique ability to stop wetness more effectively than conventional aluminum actives. Antiperspirants of this kind have come to dominate the antiperspirant market. For this reason, it is important that antiperspirant actives which improve specific aesthetic properties of the final product also have efficacy at least equal to the products being used currently and the process of making the actives be economical.

Accordingly it is an object of the present invention to provide Al/Zr antiperspirant salts over the entire range of the Final OTC Monograph that are free of amino acids or salts of amino acids and are free of polyhydric alcohols thereby improving fragrance compatibility and providing formulators wider choices in coming up with newer and better fragrances.

It is another object of the present invention to produce aluminum zirconium antiperspirant products with very low iron content that have improved compatibility with fragrance; minimize probability of the product's color change;

possibly reduce fabric staining; and minimize iron contribution to underarm area where growth of microflora, that is responsible for axillary malodour by the biotransformation of non-odorous precursors present in apocrine sweat and seabum takes place.

It is a further object of the present invention to provide novel aluminum zirconium antiperspirant products with efficacy at least equal to that of currently prevailing conventional aluminum zirconium products but at a lower cost.

It is still a further object of the present invention to produce antiperspirant products that have chromium, nickel and cobalt present in levels of each less than 2 ppm, and preferably less than 1 ppm, and iron content of less than about 30 ppm preferably less than 20 ppm and more preferably less than 10 ppm and most preferably less than 5 ppm.

BRIEF DESCRIPTION OF THE DRAWING

The FIGURE of the drawing illustrates diagrammatically the area inclusive of the aluminum zirconium products encompassed within the FDA OTC Final Monograph.

DETAILED DESCRIPTION OF INVENTION

Figure 1:
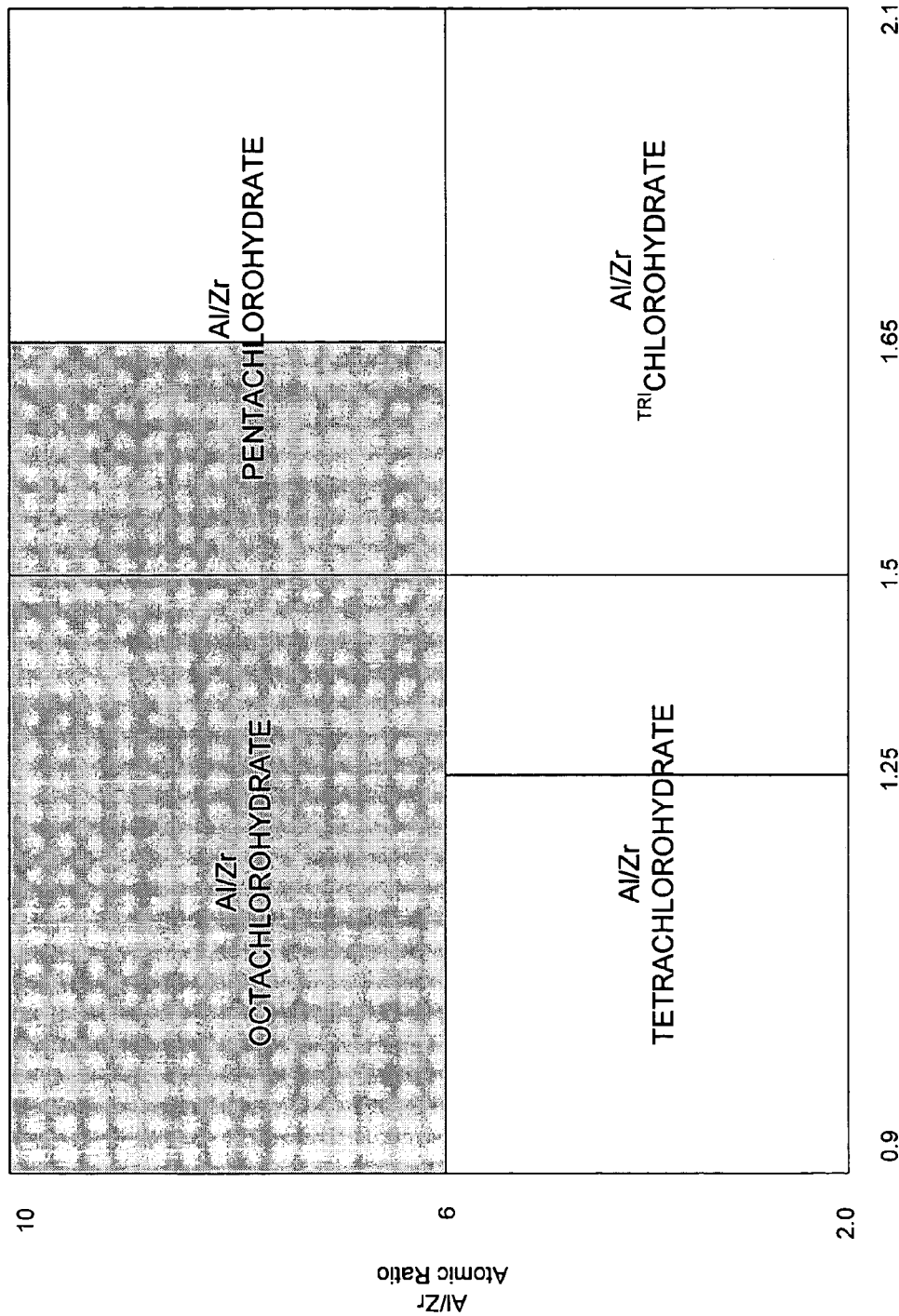

High pressure liquid chromatography (HPLC) is used to characterize macromolecular distribution of aluminum zirconium species. For details of the specific methodology used reference is made to copending patent application Ser. No. 10/807,996 filed Mar. 24, 2004.

The term "metals/chloride" ratio is used interchangeably herein with "metals/halide" ratio or "metals/anion" ratio and metals refer to (Al+Zr) or (Al+Zr+Hf) and ratio always refers to atomic ratio.

It is important to note that the weight percentage of antiperspirant salt is indicated herein as percent of anhydrous solids (% A.S.), which excludes any bound water. This is calculated in accordance with the following equation (USP 27):

% $A.S.$ in Al/Zr Salt=Al({26.98$y$+92.37+17.01[3$y$+4−($y$+1)/$z$]+35.43($y$+1)/$z$}/26.98$y$), in which Al is percentage of aluminum, y is the aluminum/zirconium atomic ratio, z is the aluminum plus zirconium/chloride atomic ratio, 26.98 is the atomic weight of aluminum, 92.97 is the atomic weight of zirconium corrected for 2% hafnium content, 17.01 is the molecular weight of the hydroxide ion (OH) and 35.453 is the atomic weight of chlorine Cl.

The percent A.S. in basic aluminum chloride salt=Al{[26.98$x$+17.01(3$x$−1)+35.453]/26.98$x$} where x is the aluminum/chloride atomic ratio.

Aluminum zirconium halides prepared in accordance with the novel method of the invention are characterized as having metals to chloride ratio between 0.9:1 to 2:1, preferably between 1.2:1 to 1.7:1 and aluminum to zirconium ratio of 2:1 to 10:1, preferably in the range of 5.5:1 to 8.5:1 and most preferably 7.5 to 8.5 to reduce cost while maintaining efficacy which is statistically not significantly different from that of aluminum zirconium tetrachlorohydrex having Al/Zr atomic ratio of about 3.5 and metal to chloride ratio of about 1.35.

The method of the present invention comprises reacting two components namely low iron basic aluminum halide solution having low trace metal (Co, Cr, Ni, Cu and Mn) impurities and represented by the empirical formula $Al_2(OH)_{6-x1}Y_{x1} \cdot nH_2O$ wherein Y is Cl, Br, or I, n is about 0.8 to 4 and 0<$x_1$<6 and a zirconium compound selected from the group having the following general empirical formula;

$ZrO(OH)_{2-nz}B_z$ and having an iron content of less than 10 ppm more preferably less than 5 ppm and wherein z may vary from 0.9 to 2 and n is the valence of B and 2-nz is greater than or equal to 0 and B is selected from the group consisting of halides.

As an alternative to or in conjunction with the above described zirconium salts, a zirconium basic carbonate represented by empirical formula $[ZrO(OH)(CO_3)_{0.5} \cdot nH_2O]$ or
$[Zr_2(OH)_4(CO_3)_2 \cdot nH_2O]$ may also be employed. However, such carbonates should not be interpreted as precise with respect to chemical structure but should be regarded only as a guide to molar ratio and wherein n represents the amount of water required to bring the equivalent $ZrO_2$ content to any specified concentration for this product; for example, for $ZrO_2$ content of about 40%, n will be about 8.7.

The basic aluminum halides may be made by a number of processes. A first preferred process is the method disclosed in U.S. Pat. No. 5,908,616 (Parekh), i.e., reacting (a) aluminum powder, (b) an aluminum halide solution and (c) water at a temperature greater than about 85° C. Another method involves mixing and reacting standard aluminum chlorohydrate with AlCl3 or HCl at a temperature from about room temperature (RT) to about reflux for a period that may range from about 0.5 hr. to about 2 hrs. The resultant solution is processed thru a ligand column to achieve iron concentration of less than 30 ppm preferably less than 20 ppm more preferably less than 10 ppm and most preferably less than 5 ppm.

In general, any standard basic aluminum halide conventionally used in the art may be used in the present method. Such solutions generally have anhydrous solids concentration of about 15% to 40%. However, it will be evident to one skilled in the art that selection of the appropriate concentration will depend upon the specific product physical and chemical properties desired. Standard basic aluminum chloride may be processed using available technologies to reduce iron content below 30 ppm preferably to below 20 ppm, more preferably to less than 10 ppm and most optimally to less than 5 ppm.

The zirconium complexes could be either low iron zirconium oxychloride solution in water or the zirconium halide complexes which can be prepared by mixing basic zirconium carbonate with hydrochloric acid or zirconium oxychloride at an elevated temperature of about 60° C.–70° C. Once a clear solution is formed, it is cooled and filtered. With aluminum halide solution of very low basicity it may be possible to use aqueous zirconium basic carbonate slurry having empirical formulas $[ZrO(OH)(CO_3)_{0.5} \cdot nH_2O]$ or $[Zr_2(OH)_4(CO_3)_2 \cdot nH_2O]$ such compounds should not be interpreted as precise with respect to chemical structure but should be regarded as a guide to molar ratio at a controlled rate such that the solution at reflux condition does not become cloudy or opaque.

The two components are reacted at a reflux temperature of about 105° C.±5° C. under closely monitored addition rate of zirconium compound, i.e., the zirconium salts, to avoid formation of cloudiness or gelation during the reaction phase. Where cloudiness develops, addition of zirconium compound is stopped until the reacting solution clears up at which time a controlled addition of the zirconium compound is resumed. Following a completion of the addition of the zirconium compound, the solution is refluxed for additional 30 to 90 minutes. If the product is to be used for clear gel or low residue antiperspirant optionally, a suitable organic solvent can be added to replace desirable amount of water by evaporation or distillation. The final solution is cooled and filtered. The final solution can be dried using any of the industrial drying methods such as spray drying. The resultant dry powder can be micronized, sieved, air-classified to achieve the desired particle size and/or shape distribution. The type of atomizer used is a function of the desired particle shape, size and density. Thus, any one of the following atomizing devices can be used for spray drying: CSC disc, two fluid nozzle, single fluid nozzle, porous metal disc or drilled hole disc.

Concentration of basic aluminum chloride and zirconium salt solution may be varied to achieve the desired anhydrous solids concentration of aluminum zirconium salt in the final solution. Lower concentrations (about 10% to about 20%) lead to higher concentration of depolymerized aluminum species similar to those of enhanced efficacy actives but they may not be stable in aqueous solutions. Such dilute solutions may be stabilized by drying within a time frame of about 10 to 24 hrs.

Iron content and other trace metal impurity level can be reduced by several available technologies. One such technology is based on a principle called molecular recognition or "host guest" chemistry. This approach resides in the use of a family of compounds (host) designed to recognize the guests and to bind them. In contrast to classical separation techniques such as precipitation, ion exchange and solvent extraction, molecular recognition technology (MRT) developed by IBC (IBC Advanced Technologies Inc., American Fork, Utah) exhibit several orders of magnitude increase in affinity and selectivity for specific elements even when these species have similar charge, shape or other attributes. Molecular Recognition Technology is a highly selective, non-ion exchange process using organic ligands that are chemically bonded to solid supports such as silica gel. The system consists of the ligand material packed into fixed bed columns that can be built in the modular form. The processing of basic aluminum chloride solution thru the ligand column results in lowering of iron concentration to less than 10 ppm. The ligand column is regenerated by elutting with dilute HCl. Concentration of iron in the treated solution can vary from less than 1 ppm to less than 20 ppm depending upon the basicity of the solution being treated and age of the column. Further reduction can be achieved by using multiple columns in series. Iron content of $5/6$ basic aluminum chloride solution (commonly known as aluminum chlorohydrate or ACH) was reduced from about 97 ppm iron to 1 ppm in one run the reduction was less than 15 ppm in a run made with the same column one week later.

Tables I and II show the results of two experimental runs made about one week apart using $5/6^{th}$ basic aluminum chloride solution. Results show significant reduction (about 85% to 99%) in iron content of the solution. As noted in these tables there were no significant changes in HPLC or chemical analysis except for the iron content.

TABLE I

Chemical Analysis of 50% ACH Solution Prior to and After Ligand Treatment

|  | Untreated | Treated | Untreated | Treated |
|---|---|---|---|---|
| % Al | 11.79 | 1.97:1 | 11.80 | 11.80 |
| % Cl | 7.86 | .69 | 7.86 | 7.86 |
| pH (as is) | 3.94 | 3.94 | 3.94 | 3.94 |
| Fe ppm | 97 | 1 | 98 | 15 |
| Al:Cl Ratio | 1.97:1 | 1.97:1 | 1.97:1 | 1.97:1 |

TABLE II

% HPLC* Peak Areas

|  | Untreated | Treated | Untreated | Treated |
|---|---|---|---|---|
| Peak I | 50.05 | 52.36 | 53.65 | 57.53 |
| Peak II | 30.42 | 27.69 | 25.99 | 24.45 |
| Peak III | 13.20 | 14.30 | 12.41 | 11.95 |
| Peak IV | 6.33 | 5.65 | 6.30 | 6.07 |

*HPLC Clumn used was Maxil RP2

Several samples of aluminum zirconium tetrachlorohydrex and trichlorohydrex were prepared using a spray dried basic aluminum chloride solution and zirconium hydroxy chloride solution available from Reheis Inc. of Berkeley Heights, N.J. The resultant powders were specifically analyzed for Pb, Ni, Co, Cr and Hg and their respective concentrations in ppm were $\leq 1.0$, $\leq 1$, $\leq 0.2 \leq 2$ and none detected (ND).

The majority of iron and other trace metal impurities in antiperspirants are primarily contributed by the aluminum metal and aluminum chloride or HCl used in the manufacture of basic aluminum chloride solutions which are the basic building blocks of all antiperspirant actives. The lower desirable values of trace metal impurities were achieved by controlling quality of raw materials and/or treatment with ligand columns.

Samples of basic aluminum chloride (BAC) powders (Microdry ACH and RE-301 SUF) and aluminum zirconium powders (Rezal® 36GP and Reach® AZP908) were prepared using untreated and ligand treated BAC solution and micronized. ΔYB values were measured (using Macbeth color spectrophotometer) for treated and untreated samples. Results showed significant improvement in yellow coloration of the powder as shown below.

|  | Untreated ΔYB | Treated ΔYB |
|---|---|---|
| Reach-301 Superultrafine | 2.3 | 0.14 |
| Microdry ACH | 0.44 | 0.10 |
| Rezal 36GP Superultrafine | 2.5 | 0.10 |
| Reach AZP-908 Superultrafine | 1.6 | 0 |

Reach-301, Microdry ACH, Rezal 36GP and Reach AZP-908 are Reheis' brand names for Reheis Inc. of Berkeley Heights, New Jersey for aluminum sesquichlorohydrate, $5/6^{th}$ basic aluminum chlorohydrate, aluminum zirconium tetrachlorohydrex and activated aluminum zirconium tetrachlrohydrex.

The following examples illustrate a novel process used to prepare low iron, glycine free aluminum zirconium actives details of which except as recited in the appended claims, are not to be construed as limitations.

EXAMPLE 1

7917 gms of basic aluminum chloride solution (% Al 9.03, % Cl 6.59) having Al/Cl atomic ratio of 1.80:1 and anhydrous solids content of 29.54% was heated to reflux temperature and 3084 gms of zirconium oxychloride (ZOC) solution (% Zr 9.45, % Cl 7.35) was added slowly to maintain clarity of the reacting solution over a 3 hour period and the solution was refluxed for one hour after the addition of ZOC was completed. The solution was filtered and analyzed. About 5100 gms of solution was spray dried at an outlet temperature of 240° F. Chemical analysis of solution and powder were as follows:

Solution % Al 6.32, % Zr 2.58, % Cl 7.11, Al/Zr atomic ratio 8.44, iron 18 ppm, M/Cl atomic ratio 1.31, pH of 15% w/w solution 3.60, % A.S. 26.44

Powder % Al 19.0, % Zr 7.85, % Cl 19.99, Al/Zr atomic ratio 8.34, iron 49 ppm, M/Cl atomic ratio 1.40. % A.S. 78.93. The micronized powder had a particle size of 97.56% less than 10 μ

EXAMPLE 2

The same procedure was followed as in Example 1 except that metals to chloride ratio was targeted to be 1.62 to make aluminum zirconium penta salt. 8670 gms of basic aluminum chloride solution having Al/Cl atomic ratio of 1.95:1 (% Al 9.66, % Cl 6.49, anhydrous solid content of 31.31%) was brought to reflux and 1670 gms of zirconium hydroxy chloride (ZHC) solution (% Zr 18.24, % Cl 12.95, Cl/Zr atomic ratio 1.86) was added over 3.25 hours and the final solution was refluxed for an additional hour. The final solution was spray dried and micronized. Chemical analysis of the solution and the powder were as follows:

Solution % Al 7.99, % Zr 2.82, % Cl 7.14, Al/Zr atomic ratio 9.75, M/Cl atomic ratio 1.62, % A.S. content 31.7%, iron 23 ppm Powder % Al 20.7, % Zr 7.32, % Cl 18.0, Al/Zr atomic ratio 9.74, M/Cl atomic ratio 1.66, anhydrous solids content 81.9%, iron 40 ppm Aluminum zirconium octa salt of example 1 was tested for antiperspirant efficacy against most widely used aluminum zirconium tetrachlorohydrex in a suspension roll-on formulation using the standard hot room procedure. In the standard hot room procedure, human volunteers are subjected to thermal stress and gravimetric determination of the perspiration produced under the thermal stress with and without antiperspirant product applications are made. The data is subjected to analysis of covariance method described by Murphy and Levine (T. D. Murphy, et al., *Analysis of Antiperspirant Efficacy Test Results*, Journal of the Society of Cosmetic Chemists, Vol. 42, May 1991, pp. 167–197) and compared for percent sweat reduction capacity. Antiperspirancy tests were conducted by an outside independent lab employing "Controlled Hot Room Gravimetric Test" in conformance with FDA guidelines.

The anhydrous suspension roll-ons were prepared using an aluminum zirconium salt concentration of about 20% on an anhydrous basis (about 25% on weight basis) and approximate concentration of other ingredients were Dow Coming 245, 70.5%, Bentone 38, 2.70%, SDA Alcohol 40 (95% alcohol+5% water) 1.8%.

Aluminum zirconium tetrachlorohydrex powder used for comparison had the following chemical analysis. % Al 14.8, % Zr 14.5, % Cl 18.36, % Glycine 11.7, Al/Zr atomic ratio 3.52 and M/Cl atomic ratio of 1.36, % A.S. 77.46.

Efficacy study was based on 37 female subjects and there was no statistically significant difference (p=0.127) in the reduction in perspiration between aluminum zirconium octachloro-hydrate having Al/Zr ratio of 8.44 and no glycine and aluminum zirconium tetrachlorohydrex having Al/Zr ratio of 3.52 with glycine. Without being bound by any theory it is hypothesized that glycine-free octa salt having Al/Zr ratio in the range of about 6.5 to 7.5 and metals/chloride ratio of about 1.20–1.25 will give about the same sweat reduction numerically as the tetrasalt (which is widely used currently), with Al/Zr ratio of about 3.5 and metals/chloride ratio of about 1.35–1.40. No adverse experiences were observed by the subjects. Sweat reduction values for the octa and tetra salts were 48% and 52% respectively. Results of this study established that amino acid free cost effective aluminum zirconium salts could be prepared without sacrificing efficacy.

It is known that fragrances in antiperspirants can discolor over time due to the acidic nature and high transition metals concentration especially Fe, Cr, Co, Mn, Cu, and Ni. It is also known that glycine can initiate Schiff base reaction with aldehydes present in fragrances. Hence, to compare novel product of this invention with the conventional aluminum zirconium tetrachlorohydrex for their ability to form color with fragrances, laboratory work was done with 14 different fragrances from nine different suppliers (Quest, Flavor & Fragrance Specialties, Shaw & Mudge Company, Firminich, Noville, Bell, Drom, Harmann & Reimer and Takasago) using samples from Examples 1, 2 and Al/Zr Tetrachlorohydrex used for efficacy testing. Fragrance dispersions were prepared as follows: 0.75% perfume, 1.0% Arlasolve 200, 20% antiperspirant active (on an anhydrous basis), q.s. DI water. Samples were stored at 45° C. for four weeks and were analyzed for color visually as well as using Macbeth Color Spectrophotometer. Aluminum zirconium tetrachlorohydrex was compared against aluminum zirconium penta and octa salts of Examples 1 and 2. Color was measured as ΔYB (yellow blue) and ΔRG (red green) for all the fourteen fragrances and three actives. Results of these measurements are shown in Table III.

While the average ΔYB and ΔRG value for all the fragrances tested are almost similar for octa and penta salts they are significantly lower than those of aluminum zirconium tetrachlorohydrex. In other words, low iron, glycine free and higher Al/Zr ratio actives of this invention are not only comparable in efficacy to the conventional product but are more fragrance friendly and less likely to form colors as intense as the conventional aluminum zirconium glycine complexes with lower Al/Zr atomic ratio. The reduction in ΔYB is about 45% and in ΔRG is about 39%.

Summarizing, based on work with 14 different fragrances (as indicated in Table III) from nine different suppliers, it can be stated that amino acid free low iron penta and octa salts having low trace metal impurities result in less discoloration then tetrasalt after four weeks of shelf aging at 45° C. The color assessments were made visually as well as instrumentally.

TABLE III

Fragrance Compatibility Study

| | ΔYB @ 45° C. | | | ΔRG @ 45° C. | | |
|---|---|---|---|---|---|---|
| Fragrance | Tetra | Penta | Octa | Tetra | Penta | Octa |
| Q-26238 | 11.51 | 6.31 | 8.49 | 8.67 | 4.69 | 7.45 |
| Q-26240 | 10.51 | 5.64 | 5.04 | 8.68 | 4.92 | 4.07 |
| Q-26241 | 11.29 | 6.60 | 7.13 | 7.98 | 3.71 | 3.76 |
| Q-26242 | 14.50 | 10.32 | 9.77 | 9.21 | 6.42 | 6.54 |
| Q-26239 | 12.12 | 8.07 | 9.40 | 8.24 | 4.93 | 6.65 |
| AC 10278/498988 | 7.12 | 4.40 | 3.77 | 4.67 | 2.30 | 1.86 |
| FFS 52847 | 8.63 | 6.70 | 6.76 | 6.48 | 6.18 | 6.37 |
| SM 25105D | 11.76 | 8.65 | 8.57 | 9.49 | 9.07 | 8.65 |
| Takasago RM 1595 | 9.49 | 9.94 | 10.02 | 9.14 | 10.38 | 10.51 |
| Quest Q-14072 | 16.59 | 12.08 | 9.61 | 14.66 | 11.30 | 10.05 |
| Firm. 430–507 | 20.27 | 13.52 | 14.63 | 18.73 | 12.66 | 12.82 |
| Noville AN 119738 | 16.28 | 13.19 | 12.23 | 16.50 | 12.92 | 11.91 |
| Bell J-8381 | 7.45 | 5.36 | 5.56 | 4.69 | 3.19 | 2.88 |
| Drom99-920 | 9.69 | 4.16 | 4.45 | 5.55 | 2.53 | 2.28 |
| Average | 11.94 | 8.21 | 8.2 | 9.48 | 6.8 | 6.84 |
| Std. Dev. | ±3.76 | ±3.16 | ±3.0 | ±4.77 | ±3.75 | ±3.59 |

Since octa-salt is more acidic than tetra- or penta-salt and as both the salts of this invention do not contain glycine, their cumulative irritation potential were compared using fourteen days of epidermal contact to the antiperspirant products being used widely at the current time. A total of twenty eight (28) subjects, male and female, were selected for this study and the study was conducted by an independent lab. The methodology used was as follows.

The upper back between the scapulae served as the treatment area. Approximately 0.2 ml of each test material (an amount sufficient to cover the contact surface), was applied to the ¾"x¾" absorbent pad portion of an adhesive dressing. These were then applied to the appropriate treatment sites to form occluded patches.

Each test material was applied to the appropriate treatment site Monday through Friday to maintain fourteen consecutive days of direct skin contact. Patches applied on Friday remained in place until the following Monday. Evaluations of the test sites were conducted prior to each patch application.

If a test has been observed to exhibit an evaluation score of a "3", the application of test material to this site would have been discontinued and the observed score of "3" would be recorded for the remaining study days.

The following scoring procedure was used

0—No visible skin reaction

+—Barely perceptible or spotty erythema

1—Mild erythema covering most of the test site

2—Moderate erythema, possible presence of mild edema

3—Marked erythema, possible edema

4—Severe erythema, possible edema, vesiculation, bullae and/or ulceration

The compounds selected for the study were aluminum zirconium octa chlorohydrate and penta chlorohydrate salt solutions, 50% aluminum chlorohydrate solution, activated aluminum zirconium tetrachlorohydrex solution as control. Chemical analysis of the samples are shown in Table IV.

TABLE IV

| Product | Al/Zr Octa Chlorohydrate | Al/Zr Penta Chlorohydrate | Activated Al/Zr Tetrachloro-hydrate | 50% ACH Solution |
|---|---|---|---|---|
| % Al | 6.43 | 8.02 | 7.34 | 11.86 |
| % Zr | 2.7 | 3.11 | 6.12 | 0 |
| % Cl | 7.33 | 7.60 | 9.01 | 8.07 |
| % Gly | 0 | 0 | 5.04 | 0 |
| Al/Zr | 8.21 | 8.89 | 4.13 | — |
| M/Cl | 1.29 | 1.54 | 1.33 | 1.93 |
| % A.S. | 27.1 | 32.53 | 36.51 | 38.49 |
| pH 15% w/w | 3.76 | 4.08 | 3.93 | 4.41 |
| pH as is | 3.15 | 3.18 | 3.16 | 3.75 |

All the aluminum zirconium salt solution for irritancy test were prepared based on 20% anhydrous solids concentration except for 50% ACH solution which was based on 23% anhydrous solids.

Results of the 14-day cumulative irritation patch study are summarized in Table V below.

TABLE V

| Active* | pH (15% w/w) | CIT Score |
|---|---|---|
| Rezal 885 Solution (Al/Zr octa salt soln.) | 3.76 | 0.5 |
| Rezal 95 Solution (Al/Zr penta salt soln.) | 4.08 | 0.0 |
| Reach AZP-908 Concentrate (Al/Zr tetra salt soln.) | 3.93 | 0.0 |
| Chlorhydrol 50% Solution (ACH soln.) | 4.41 | 0.0 |

The cumulative irritation test is most sensitive to small differences between test materials. Results show that octa- and penta-salt without glycine do not show higher irritancy potential than the compounds most widely used, like aluminum zirconium tetrachlorohydrex and aluminum chlorohydrate (ACH).

As noted heretofore, different forms of finished formulations require antiperspirant actives with different chemical and physical properties. For clear gel emulsion it is desirable to have an active with a specific refractive index (RI), less water to achieve specific aesthetic and certain solubility requirements. It is also desirable that the organic solvent used does not impart "tackiness" to the final formulation. The following examples demonstrate preparation of amino acid free Al/Zr actives for less or non-tacky clear gel or clear stick. The spray dried product can be used for low or no residue opaque antiperspirant stick.

EXAMPLE 3

2500 gms of aqueous solution of basic aluminum chloride (BAC) having chemical analysis of 11.8% Al, 9.11% Cl, Al:Cl atomic ratio of 1.7 and anhydrous solids content of 38.86 was heated in a three neck round bottom flask using a heating mantal equipped with a rheostat for temperature control. The flask was equipped with a reflux condenser, a separator addition funnel to add zirconium salt solution at a controlled rate and was fitted with an overhead stirring device. The BAC solution was heated to a reflux temperature. 1300 gms of zirconium hydroxy chloride (ZHC) solution (prepared by reacting zirconyl oxychloride (ZOC) with zirconium basic carbonate at 60° C.) having chemical composition of 22.7% Zr, 11.58% Cl, Cl/Zr atomic ratio of 1.33 was added dropwise using the addition funnel over four hours. ZHC solution addition rate was controlled to assure that the solution remained clear during the entire addition. At the completion of ZHC addition, 1100 gms of dipropylene glycol (DPG supplied by Dow Chemical) was added and 600 gms of water was distilled off over 1.5 hrs. The solution was cooled to room temperature and filtered off giving a crystal clear solution. The chemical analysis and some of the physical properties of the final solution were as follows:

% Al 6.95, % Zr 6.91, % Cl 8.92, pH 15% w/w solution 3.76, % DPG 25.94, % A.S. 36.7, Al/Zr atomic ratio 3.47, M/Cl atomic ratio 1.32, viscosity 248 cps, RI at 21° C. 1.4513.

This anhydrous solution is suitable for use in a clear gel emulsion and low or no residue or clear stick formulation.

EXAMPLES 4, 5, AND 6

The same equipment set up and procedure of Example 3 were followed for Examples 4, 5, and 6 except for the use of different organic solvents and chemical analysis of ingredients as listed in Table VI.

TABLE VI

| | Example 4 | Example 5 | Example 6 |
|---|---|---|---|
| Chemical analysis of BAC solution used | Al 11.8%, Cl 9.11% Al:Cl ratio 1.7:1 % AS 38.86 | Same as Example 4 | Same as Example 4 |
| Chemical analysis of ZHC solution used | Zr 23.34% Cl 12.13% Cl/Zr 1.37:1 % A.S. 46.73 | Same as Example 4 | Same as Example 4 |
| Organic Solvent used | Polyethylene glycol 200 (PEG 200) supplied by Dow Chemical | Polyethylene glycol-400 (PEG 400) supplied by Dow Chemical | Glycerin (USP grade supplied by Callahan Chemical Co.) |

Results of chemical analysis, HPLC and physical properties for Examples 4, 5 and 6 are shown in Table VII.

TABLE VII

| | Example 4 | Example 5 | Example 6 |
|---|---|---|---|
| Polyol | PEG - 200 | PEG - 400 | Glycerin |
| % Al | 6.8 | 7.06 | 6.8 |
| % Zr | 6.89 | 6.92 | 6.23 |
| % Cl | 8.69 | 8.9 | 8.21 |
| % Polyol | 25 | 22.47 | 11.2 |
| Fe(ppm) | 20 | 20 | 17 |
| pH 15% (w/w) | 3.7 | 3.74 | 3.69 |
| Viscosity CPS* | 450 | 1000 | 40 |
| RI° 21° C.* | 1.4543 | 1.4527 | — |
| Al/Zr Atomic Ratio | 3.4 | 3.51 | 3.76 |
| M/Cl Atomic Ratio | 1.33 | 1.34 | 1.38 |
| % A.S. | 36.1 | 37 | 34.7 |
| HPLC (Initial) (Band I/II/III/IV) | 32.13/25.47/ 12.06/30.34 | 32.45/22.49/ 13.69/31.37 | 36.47/21.73/ 10.15/30.23 |
| HPLC (After 55 days of aging at RT) | 32.76/22.13/ 8.89/36.22 | 37.19/22.24/ 8.47/32.10 | 36.99/22.05/ 10.29/30.67 |

*Viscosity was measured using Brookfield viscometer spindle # 2 at 30 or 60 rpm and reading was taken after 5 minutes. RI was measured using Leica refractometer model #10500.

Conventional enhanced antiperspirant salt would ordinarily lose peak ratio rapidly in aqueous solution. Thus, stability of enhanced efficacy active is usually measured by the degree of degradation of Band III/II peak area (or peak 4/peak 3 peak area) ratio. By stabilized or stable it is meant that Band III/II peak area ratio while it may degrade somewhat it will not degrade quickly to as low a point as an unenhanced salt. A review of the prior art shows that the known enhanced efficacy salts have HPLC Band III/II area ratio of about 0.5 or higher, in contrast, conventional non-enhanced antiperspirant salt have area of about 0.2 or less. (Ref. U.S. Pat. No. 6,436,381 B1, Col. 1, 40–50)

To check stability of the aluminum zirconium salt solution prepared by the novel process of this invention HPLC of samples prepared under Examples 4, 5 and 6 were monitored initially and after about 55 days and ratio of Band III/II were compared. Results are shown in Table VIII. The products exhibited good stability over almost two months.

TABLE VIII

| | % HPLC Peak Areas | | | | | |
|---|---|---|---|---|---|---|
| Peak Area Ratio | Example 4 Initial | Example 4 After Aging + | Example 5 Initial | Example 5 After aging + | Example 6 Initial | Example 6 After Aging + |
| Band III/II | 0.47 | 0.40 | 0.61 | 0.38 | 0.5 | 0.5 |

+ Aged for about 2 months at room temperature.

Although the present invention has been described in terms of specific embodiments, the invention is not meant to be so limited. Various changes can be made to the composition and proportions used while still obtaining the benefits of the invention. Thus the invention is only to be limited by the scope of the appended claims.

What is claimed is:

1. A process for preparing stable, low iron, amino acid free aluminum zirconium aqueous antiperspirant compositions having a trace impurity level of each metal (Co, Cr, Ni, Mn, Cu) of less than 2 ppm and having an anhydrous solids content of at about 25% to about 35% which comprises:

(i) heating aqueous solution of a low iron basic aluminum halide compound having an iron content of less than 30 PPM and having anhydrous solids content up to and including about 44% and represented by the general empirical formula

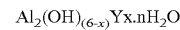

$Al_2(OH)_{(6-x)}Y_x \cdot nH_2O$ wherein Y is Cl, Br, or I and $0 \leq x \leq 6$ and n is about 0.8 to 4 and at reflux temperature;

(ii) admixing said compound at reflux with an amino acid free zirconium compound at a rate to maintain the refluxing solution substantially clear, said zirconium compound being selected from (a) those having the general formula

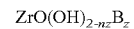

$ZrO(OH)_{2-nz}B_z$ wherein z may vary from 0.8 to 2 and n is the valance of B and 2-nz is greater than or equal to 0 and B is selected from the group consisting of halides or nitrate; (b) those having the formula

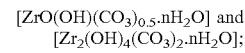

$[ZrO(OH)(CO_3)_{0.5} \cdot nH_2O]$ and
$[Zr_2(OH)_4(CO_3)_2 \cdot nH_2O];$ (iii) refluxing the admixed solution for about 1–2 hours following the completion of the addition of zirconium compound, (iv) cooling the solution to room temperature,
(v) and filtering it to give a clear aqueous solution of an antiperspirant salt.

2. The process of claim 1 wherein the low basic aluminum halide compound has an iron content of less than 20 ppm.

3. The process of claim 1 wherein the low basic aluminum halide compound has an iron content of less than 10 ppm.

4. The process of claim 1 wherein the low basic aluminum halide compound has an iron content of less than 5 ppm.

5. The process of claim 1 wherein the refluxed substantially clear reaction product before step (iv) is admixed with a polar organic solvent selected from the group consisting of dihydric or polyhydric alcohol, or low molecular weight polyethylene glycol (having a molecular weight less than 600) or glycerin and mixtures thereof and removing excess water by distillation or evaporation to yield the final aqueous antiperspirant solution having at least 30% anhydrous solids content of aluminum zirconium salt and organic solvent.

6. The process of claim 1 wherein the basic aluminum halide is low iron basic aluminum chloride and the zirconium compound is low iron zirconium oxychloride.

7. The process of claim 5 wherein in the low iron basic aluminum halide is basic aluminum chloride and the zirconium compound is zirconium hydroxychloride.

8. The process of claim 1 in which basic aluminum halide solution is treated with a ligand column or equivalent technology to reduce the iron content to the desired level.

9. The process of claim 1 in which trace metal impurity level of each metal Ni, Cr, Co, Mn, Cu is less than 2 ppm and preferably less than 1 ppm.

10. The process of claim 1 wherein the aluminum zirconium antiperspirant active Al/Zr ratio is from about 2:1 to about 10:1 and the metals to chloride ratio is from about 0.9:1 to 2:1.

11. An antiperspirant composition prepared according to the process of claim 1 where Al/Zr ratio is 3:1 to 7:1 and metal to chloride ratio is 1.25:1 to 1.45:1.

12. An antiperspirant composition prepared according to the process of claim 1 where Al/Zr ratio is 3:1 to 7:1 and metal to chloride ratio is 1.5:1 to 1.8:1.

13. The process of claim 5 wherein the polar organic solvent is selected from dipropylene glycol, polyethylene glycol (with molecular weights less than 600), tripropylene glycol, propylene glycol, methoxy propanol, propylene glycol methyl ether, dipropylene glycol methyl ether and glycerin and mixture thereof.

14. The process of claim 5 wherein the polar organic solvent is polyhydric alcohol having at least three to about 12 carbon atoms and at least two hydroxy groups and is present at a concentration of 5 to 50 weight percent.

15. The process of claim 1 wherein the filtered solution obtained by step (v) is spray dried.

16. The process of claim 5 wherein the filtered solution of step (v) is spray dried.

17. The process of claim 15 wherein the dried product is micronized to have an average particle size of about 1 to 15 microns.

18. The process of claim 16 wherein the dried product is micronized to have an average particle size of about 1 to 15 microns.

19. A product prepared according to the process of claim 15 wherein the dried powder has a loss on drying when kept at 105° C. for 2 hrs. from 5% to 20% by weight.

20. A product prepared according to the process of claim 16 wherein the dried powder has a loss on drying when kept at 105° C. for 2 hrs. from 5% to 20% by weight.

21. A product prepared according to the process of claim 15 wherein the critical humidity of the product is about 5%–20%.

22. A product prepared according to the process of claim 16 wherein the critical humidity of the product is about 5%–20%.

23. An antiperspirant "roll on" or "clear gel" formulation in which the active ingredient solution is prepared according to the process of claim 1.

24. An antiperspirant "roll on" or "clear gel" formulation in which the active ingredient solution is prepared according to the process of claim 5.

25. An anhydrous antiperspirant "roll on" or "clear gel" formulation in which the active ingredient solution is prepared according to the process of claim 17.

26. An anhydrous antiperspirant "roll on" or "clear gel" formulation in which the active ingredient solution is prepared according to the process of claim 18.

27. The antiperspirant active prepared according to the process of claim 1 wherein the anhydrous solids concentration is at least 10% and no more than 20% and the solution is spray dried in less than 24 hours.

28. The antiperspirant active prepared according to the process of claim 5 wherein the anhydrous solids concentration is at least 10% and no more than 20% and the solution is spray dried in less than 24 hours.

29. The antiperspirant active prepared according to the process of claim 28 where band III/II peak area ratio is at least 0.4 and band IV peak area is at least 30%.

30. The clear anhydrous antiperspirant solution obtained by dissolving antiperspirant powder of claim 16 in an organic solvents of claim 13.

31. The clear anhydrous antiperspirant solution obtained by dissolving antiperspirant powder of claim 16 in an organic solvents of claim 14.

* * * * *